United States Patent [19]

Arms

[11] Patent Number: 4,964,862
[45] Date of Patent: Oct. 23, 1990

[54] METHOD OF AND MEANS FOR MEASURING LIGAMENT TENSION

[75] Inventor: Steven W. Arms, Burlington, Vt.

[73] Assignee: Micro Strain Company, Burlington, Vt.

[21] Appl. No.: 401,221

[22] Filed: Aug. 31, 1989

[51] Int. Cl.⁵ .......................... A61F 5/00; A61F 2/08
[52] U.S. Cl. .................................. 606/102; 606/103; 623/13
[58] Field of Search ......... 128/92 V, 92 VD, 92 VK, 128/92 VL, 92 R; 623/13; 606/53, 80, 96, 97, 67, 69, 74, 103, 71, 102

[56] References Cited

U.S. PATENT DOCUMENTS

| | | | |
|---|---|---|---|
| 4,301,551 | 11/1981 | Dore | 623/13 |
| 4,597,766 | 7/1986 | Hilal | 623/13 |
| 4,712,542 | 12/1987 | Daniel | 623/13 |
| 4,739,751 | 4/1988 | Sapega | 128/92 V |
| 4,773,910 | 9/1988 | Chen | 623/13 |
| 4,834,752 | 5/1989 | Van Kampen | 623/13 |
| 4,851,005 | 7/1989 | Hunt | 623/13 |

Primary Examiner—Robert A. Hafer
Assistant Examiner—Michael Brown
Attorney, Agent, or Firm—Thomas N. Neiman

[57] ABSTRACT

The novel ligament tension measuring device has a looped prosthetic ligament or sutures that surround a receptacle. The receptacle contains a positioning hole that allows a fixation pin to be inserted to obtain the optimum position for the desired process. The receptacle also has measuring devices, such as strain gauges or magnets and hall effect sensors. The method includes the steps of: preparing to attach the ligament to the bone; placing the device into the loop of the ligament at the tibia; adjusting the tension on the measuring device; temporarily attaching the ligament at the desired position; pinning the device in place; moving the knee through the entire range of motion; repositioning the device as necessary for the optimum position; removing the device, while leaving the pin in position; and proceeding with the permanent attachment of the ligament.

5 Claims, 2 Drawing Sheets

METHOD OF AND MEANS FOR MEASURING LIGAMENT TENSION

This invention pertains to measurement devices, and in particular to such measurement devices that relate to the measurement of ligament tensions for use during surgical procedures for ligament replacement.

Devices that measure tension of the ligament are well known to those in the surgical prosthetic field, especially to those who are dealing with surgical ligament replacement. One of the main difficulties with the current procedures is that most of the devices are fairly large and require large openings or a series of openings in order to function properly. It would be highly desirable to develop a miniature sensor to eliminate many of the disadvantages of the previous mechanisms. Examples of some of these mechanisms can be seen in the Acufex Isometric Positioner. This device requires the use of a large position pointer and a knurled centering knob to measure the isometric point; that is, the hole entry sites within the knee which allow the knee to go through a complete range of motion with minimum changes of length. In order to fix the ligament to bone, the surgeon must hold the tensioning device, pull while reading the scale, and then try to guess the exact placement of the screw in the bone in order to maintain the ideal tension.

The difficulties that are inherent in these designs and should be overcome include the following: large sizing of the equipment; the inability to temporarily attach the device to test the tension and adjust it as necessary; lack of a continuous tension reading; and the inability to have the specific attachment point be maintained.

Clearly, it is desirable for a means for measuring ligament tension that can easily be used with permanent ligament prosthesis shown in the U.S. Patent issued to Chen et. al., No. 4,773,910 on 27 Sept. 1988. It is the object of this invention, then to set forth a means for and method of measuring ligament tension which avoids the disadvantages and limitations, above-recited, which occur in previous measuring devices. It is another object of this invention to teach a device that has a small geometry and provides a continuous readout for said means.

It is also the object of this invention to teach a means for measuring ligament tension which is simple to install and use and that will enable the surgeon to easily determine the exact placement of the drill hole for permanent attachment. Particularly, it is the object of this invention to set forth means for measuring ligament tension, for use during surgical procedures for ligament replacement, comprising retaining means; said retaining means comprising at least one looped flexible strand; receptacle means being enveloped within said retaining means; said receptacle means having an aperture located therein; said receptacle means further having measurement means; monitoring means for continuously measuring the ligament tension; and position setting means. It is another object of this invention to teach a method of measuring ligament tension, for use during surgical procedures for ligament replacement, comprising the steps of: preparing to attach the ligament to the bone; placing the means for measuring ligament tension into the loop of the ligament at the tibia; adjusting the tension on said means while continuously monitoring the tension; temporarily attaching the ligament at the desired position; pinning said means in place; moving the knee throughout the entire range of motion; repositioning said means as necessary to obtain the optimum position; removing said means, while leaving the pin in the optimum position and proceeding with the permanent attachment of the ligament.

Further objects and features of this invention will become more apparent by reference to the following description taken in conjunction with the accompanying figures, in which.

Figure 1:
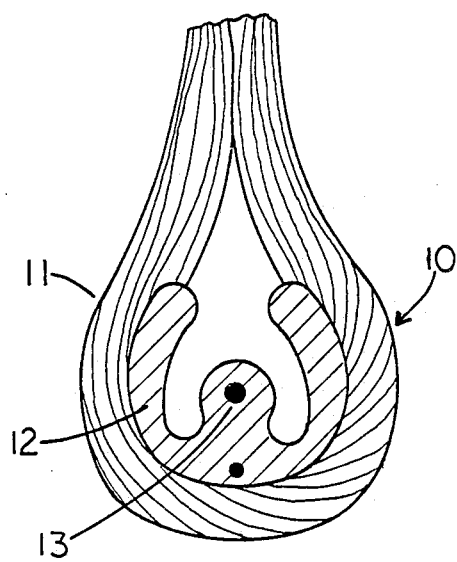
FIG. 1 is a top view of the novel ligament tension measuring means.
Figure 2:
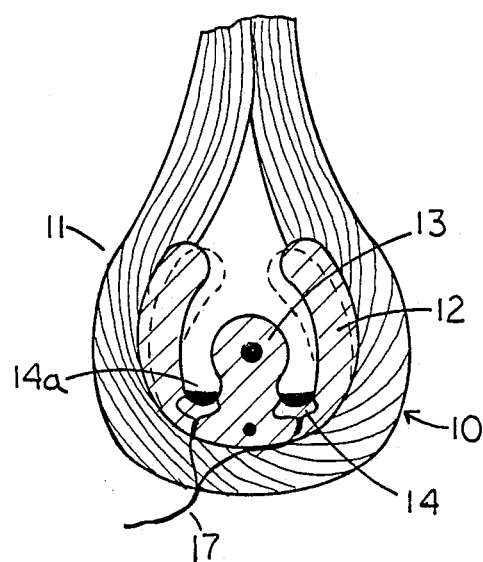
FIG. 2 is a top view of the novel means with strain gauges in position, showing the compression of the receptacle.
Figure 3:
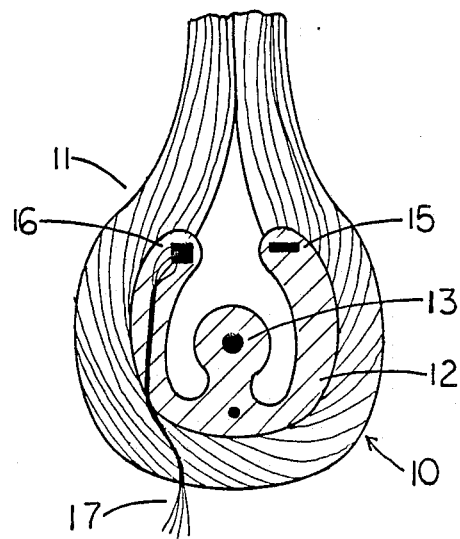
FIG. 3 is a top view of the novel means with a hall effect sensor and magnet in position.
Figure 4:
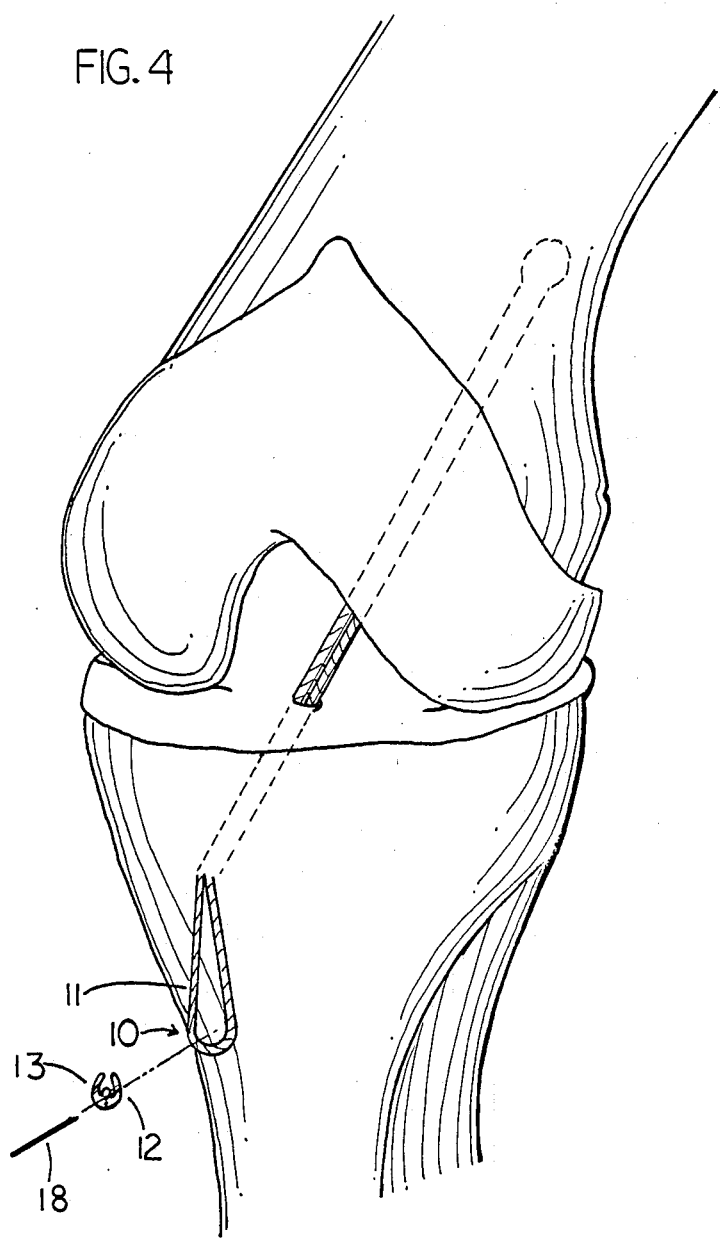
FIG. 4 is a perspective view of the novel means in position in the knee.
Figure 5:
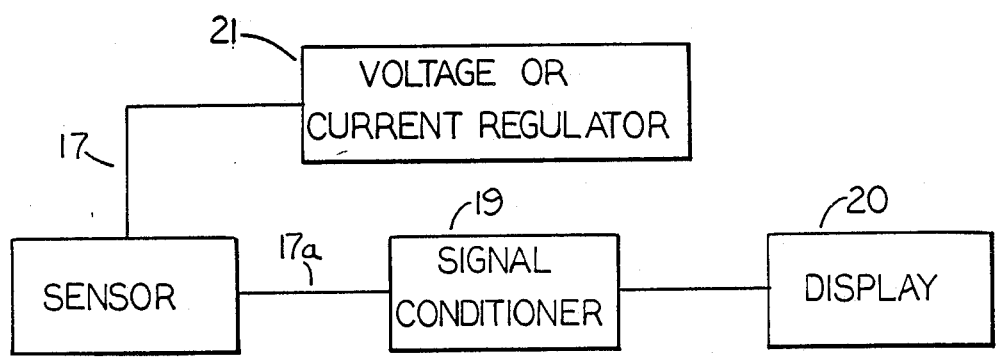
FIG. 5 is a schematic block drawing of the voltage or current regulator, signal conditioner and display.

As shown in the figures, the novel tension measuring means 10 is comprised of looped prosthetic ligament or suture 11 which surrounds a compressible implantable receptacle 12. The receptacle contains a positioning hole 13 and a measuring device. The measuring device can be in the form of a pair of strain gauges 14 and 14a, bonded to the receptacle 12 where resistance changes as a result of the deformation of the receptacle 12. In an alternative embodiment, a magnet 15 and hall effect sensor 16 act as measurement devices to measure the changes in their relative positions to each other when compressed. Electrical connections 17 from the regulator 21 provide constant voltage or current to the strain gauges 14 and 14a or the hall effect sensor 16. Electrical connections 17a connect the sensors to a signal conditioner 19, which in turn connects to a display device 20 in order to provide a continuous readout of the tension being measured. A fixation pin 18 is used to temporarily attach the means 10 in position and then, the pin is left in when the means are removed to pinpoint the exact location for permanent attachment of the ligament.

The novel method comprises the steps of:
preparing to attach the ligament to the bone;
placing the means for measuring ligament tension into the loop of the ligament at the tibia;
adjusting the tension on the device while continuously monitoring the tension;
temporarily attaching the ligament at the desired position;
pinning the device in place;
moving the knee throughout the entire range of motion;
repositioning the device as necessary to get the optimum position;
removing the device, while leaving the pin in the optimum position; and
proceeding with the permanent attachment of the ligament.

In operation, the surgeon prepares to attach the ligament to the bone. He would place the tensiometer within the loop at the end of the prosthetic ligament or suture at the tibia. The device can be held by placing a loop of wire or suture through the aperture in the receptacle and pulling it as necessary to get the desired reading on the readout unit. This aperture is located adjacent to the positioning hole. When the reading is measured, the device is brought to rest against the tibia and a small pin is placed in the positioning hole of the receptacle to mark the location of the attachment of the ligament. The knee can then be moved through several ranges of motion and the varying tensions can be measured by the readout device. If the position is not ideal the pin can be removed to another location, until the ideal site is identified. Once the ideal location is identified, the device can be removed, leaving the pin in position. The proper drill is then used to place the washer, screw and ligament assembly into position in the tibia.

While I have described my invention in connection with specific embodiments thereof, it is clearly to be understood that this is done only by way of example and not as a limitation to the scope of my invention as set forth in the objects thereof and in the appended claims.

I claim:

1. Means for measuring ligament tension, for use during surgical procedures for ligament replacement, comprising:
   retaining means;
   said retaining means comprising at least one looped flexible strand;
   implantable receptacle means being enveloped within said retaining means;
   said implantable receptacle means having a position aperture located therein;
   said implantable receptacle means further having measurement means;
   monitoring means for continuously measuring the ligament tension;
   said monitoring means having flexible lead wire circuitry from said measuring means for (a) delivering excitation to said measuring means, and (b) conducting said signals from said measuring means to conditioning electronic means and to a continuous display of tension;
   position setting means; and
   said position setting means comprising a fixation pin placed through said position aperture located within said implantable receptacle means.

2. Means for measuring ligament tension, according to claim 1, wherein:
   said looped flexible strands comprising a prosthetic ligament.

3. Means for measuring ligament tension, according to claim 1, wherein:
   said implantable receptacle means comprising a compressible u-shaped structure manufactured of a material possessing a high modulus of elasticity with a predetermined structural thickness.

4. Means for measuring ligament tension, according to claim 1, wherein:
   said measuring means comprising strain gauges located within said receptacles; and
   said strain gauges comprising piezo-resistive materials, such as constantan foil bonded to said implantable receptacle.

5. A method of measuring ligament tension, for use during surgical procedures for ligament replacement, comprising the steps of:
   preparing to attach the ligament to the bone;
   placing the means for measuring ligament tension into the loop of the ligament at the tibia;
   adjusting the tension on said means while continuously monitoring the tension;
   temporarily attaching the ligament at the desired position;
   pinning said means in place;
   moving the knee throughout the entire range of motion;
   repositioning said means as necessary to obtain the optimum position for permanently anchoring the ligament at a predetermined tension;
   removing said means, while leaving the pin in the optimum position; and
   proceeding with the permanent attachment of the ligament.

* * * * *